US005747006A

United States Patent [19]

Dornoff et al.

[11] Patent Number: 5,747,006
[45] Date of Patent: May 5, 1998

[54] SKIN WHITENER COMPOSITION CONTAINING ACEROLA CHERRY FERMENTATE

[75] Inventors: Jeffrey M. Dornoff, Grand Rapids; Deborah A. O'Toole, Ionia, both of Mich.; Michael B. Davies, Chattanooga, Tenn.

[73] Assignee: Amway Corporation, Ada, Mich.

[21] Appl. No.: 856,433

[22] Filed: May 14, 1997

[51] Int. Cl.$^6$ ..................................................... A61K 7/48
[52] U.S. Cl. ..................... 424/62; 514/474; 424/195.1; 424/78.03; 424/115; 424/123
[58] Field of Search ........................... 514/474; 435/813, 435/853; 424/195.1, 78.03, 115, 123

[56] References Cited

U.S. PATENT DOCUMENTS

| | | | |
|---|---|---|---|
| Re. 33,993 | 7/1992 | Grollier et al. | 424/74 |
| 3,012,942 | 12/1961 | Morse | 514/474 |
| 3,012,943 | 12/1961 | Morse | 435/267 |
| 3,086,915 | 4/1963 | Morse | 435/267 |
| 4,278,656 | 7/1981 | Nagai et al. | 424/62 |
| 4,369,174 | 1/1983 | Nagai et al. | 424/62 |
| 4,722,843 | 2/1988 | Vinson | 424/195.1 |
| 4,806,365 | 2/1989 | Nakashima | 426/17 |
| 4,851,252 | 7/1989 | Greither et al. | 426/599 |
| 4,877,627 | 10/1989 | Leitz et al. | 426/285 |
| 4,919,921 | 4/1990 | Hatae | 424/62 |
| 5,171,571 | 12/1992 | Stephan et al. | 424/195.1 |
| 5,262,153 | 11/1993 | Mishima et al. | 424/60 |
| 5,262,162 | 11/1993 | Bormann et al. | 424/195.1 |
| 5,281,196 | 1/1994 | Sultenfuss | 424/401 |
| 5,296,500 | 3/1994 | Hillebrand | 514/562 |
| 5,427,775 | 6/1995 | Sakai et al. | 424/62 |

FOREIGN PATENT DOCUMENTS

| | | |
|---|---|---|
| 2 597 337 | 10/1987 | France . |
| 62-208236-A | 9/1987 | Japan . |
| 62-208267-A | 9/1987 | Japan . |
| 2-200610 | 8/1990 | Japan . |
| 5-207865-A | 8/1993 | Japan . |
| H7-61915 | 3/1995 | Japan . |

OTHER PUBLICATIONS

Search results from Teltech® Literature Search Service re Skin Whiteners, Apr. 4, 1996, pp. 1–49.

*Report of a Case of Acute Infant Scurvy Treated with Acerola Jelly*, C.F. Asenjo Ph. D. and O. Gonzalez–Alvarez, M.D., 1955.

*Ascorbic Acid Content and Other Characteristics of the West Indian Cherry*, Conrado F. Asenjo and Carlos G. Moscoso, Department of Chemistry and Nutrition School of Tropical Medicine and Department of Plant Breeding, Agricultural Experiment Station, University of Puerto Rico, Food Research, vol. 15, Jan.–Dec., 1950, pp. 103–106,.

*Acerola Juice Ready for Commercial Production*, Journal of Agricultural and Food Chemistry, Nov. 10, 1954, vol. 2, No. 23, p. 1155.

*Skin Lightening, A review of melanin formation and the isolation of a new ingredient for products that minimize skin discolorations due to excessive melanin production*, Ok–Sub Lee, Eun–Joung Kim, Cosmetics & Toiletries® magazine, vol. 110, Oct. 1995, pp. 51–56.

Chemical Abstract, No. 122(21)264022r, *Kinetics Of Anthocyanin Decomposition In Acerola Juice*, Author(s): Harvey T. Chan, Jr., and Harry Y. Yamamoto, Journal: ASEAN Food J., 1994, vol. 9, No. 4, pp. 132–135.

Chemical Abstract, No. 121(17)198461j, *Effects Of Growth Regulators Applied At Blooming Time On Fruit Quality Of Acerola, Malpighia emerginata dc.*, Author(s) Kiyotake Ishihata and Saburo Ito, Journal: Nettai Nogyo, 1994, vol. 38, No. 2, pp. 113–118.

Chemical Abstract, No. 120(23) 297204(p), *Nutrient–Supplying Foods Containing Vitamin C*, Inventor (Author): Togo Kuroiwa; Patent: Japan Kokai Tokkyo Koho; JP 9422727 A2; dated Feb. 1, 1994.

Chemical Abstract, No. 120(17) 215777r, *Acerola Juice as Acidulant in Preparation of Frozen Desserts*, Inventor (Authors): Hiroshi Yamane; Teruaki Myazaki and Kyoshi Takada; Japan Kokai Tokyo Koho JP 93344846 A2; dated Dec. 27, 1993.

Chemical Abstract, No. 120(16) 200486w, *Dialysis System for Large Intestine, Method of Use, and Filtrate Solution Composition*, Inventor (Author): Andrew Stone, Patent: PCT International WO 9403215; dated Feb. 17, 1994.

Chemical Abstract, No. 120(11)132676f, *Volatile Constituents of Acerola*, C. Schippa, G. George, R. Fellous, Journal: Parfums, Cosmet., Aromes; 1993, vol. 113, pp. 81–84.

Chemical Abstract, No. 119(23)248618x, *Vitamin C–High Nutrition Supplements Preparation from Acerola Fruits*, Inventor (Author) Togo Kuroiwa, Patent: Japan Kokai Tokyo Koho JP 93207865 A2, dated Aug. 20, 1993.

Chemical Abstract, No. 118(23)2733z, *Carotenoid–Containing Emulsions for Use in Foods Without the Use of Synthetic Agents*, Inventor (Author) Lance Elliott Schlipalius, Patent: PCT International WO 9304598 A1; dated Mar. 18, 1993.

Chemical Abstract, No. 118(21) 211546a, *Calculation of Juice Content in a Diluted Fruit Juice Beverage*, Chester W. Lindsay, Journal: J. AOAC Int., 1993, vol. 76, No. 2, pp. 424–430.

(List continued on next page.)

*Primary Examiner*—Thurman K. Page
*Assistant Examiner*—Lakshmi Channavajjala
*Attorney, Agent, or Firm*—Brinks Hofer Gilson & Lione; G. Peter Nichols

[57] ABSTRACT

A skin whitening composition includes acerola cherry fermentate. The composition can be topically applied to the human skin and can include one or more whitening agents in combination with acerola cherry fermentate to achieve enhanced whitening effect. A method of whitening human skin includes topically applying to the skin acerola cherry fermentate in an amount and for a period of time sufficient to visibly whiten the skin. The method includes incorporating acerola cherry fermentate with known whitening agents and applying to the skin in an amount and for a period of time sufficient to visibly whiten the skin.

9 Claims, No Drawings

OTHER PUBLICATIONS

Chemical Abstract, No. 118(1)5952b, *Analysis of Acerola*, Authors: Shintetu Kuniyoshi, Minoru Suzuki and Hiromichi Hayano, Journal: Kanzei Chuo Bunsekishoho; 1992, vol. 31, pp. 81–85.

Chemical Abstract, No. 117(17)169813n, *The Ascorbic Acid Contents of Fruits of Taiwan*, Authors: Huei Ing Liu, and Iuan Huei Hwang, Journal: Zhonghua Nongye Yanjiu; 1991, vol. 40, No. 3, pp. 280–290.

Chemical Abstract, No. 115(25)278390b, *Change in Vitamin C During the Fermentation of Acerola Vinegar*, Makoto Nakamura, Journal: Nippon Shokuhin Kogyo Gakkaishi, 1991, vol. 38, No. 8, pp. 691–694.

Chemical Abstract, No. 114(19)184032p, *Ascorbic Acid Content in Acerola Fruit From Different Production Regions in Relation to Degree of Maturity and Its Stability During Processing*, Author(s): Saburo Itoo, Mitsuko Aiba, Kiyotake Ishihata; Journal: Nippon Shokuhin Kogyo Gakkaishi; 1990, vol. 37, No. 9, pp. 726–729.

Chemical Abstract, No. 114(18)170990n, *Water Purifying Agent*, Inventor (Author) Norio Someya, Patent: Japan Kokai Tokyo Koho JP 90268885A2; dated Nov. 2, 1990.

Chemical Abstract, No. 110(23)211306(g), *Vinegar Enriched With Vitamin C and Its Manufacture*, Inventor (Author) Todomu Nakashima, Patent: United States Pat. No. 4,806,365 dated Feb. 21, 1989.

Chemical Abstract, No. 108(26)226675j, *Cosmetic Containing Antioxidants to Delay the Aging of Skin*, Inventor (Author) Olivier Courtin, Patent: French Patent No. FR 2597337 dated Oct. 23, 1987.

Chemical Abstract, No. 104(25)223741j, *Pesticide Tolerances for Glyphosate*, Corporate Author: United States Environmental Protection Agency, Journal: Federal Regist., 1986, vol. 51, No. 78, pp. 15325–15326.

Chemical Abstract, No. 100(9)66734g, *Pesticide Programs, Tolerances for Pesticide Chemicals in or on Raw Agricultural Commodities*, Paraquat, Corporate Author: United States Environmental Protection Agency, Journal: Fed. Regist., 1984, vol. 49, No. 4, p. 882.

Chemical Abstract, No. 72(13)65961v, *Root Development of Acerola Trees as Affected by Liming*, Authors: Ernesto Hernandez–Medina, J. Velez–Santiago, M.A. Lugo–Lopez, Journal: J. Agr. Univ. P.R., 1970, vol. 54, No. 1, pp. 57–61.

Chemical Abstract, No. 68(1)2091h, *Observations on Physical and Chemical Properties of Acerola Fruit and Puree*, Author: Brian Ian Brown, Journal: Queensl. J. Agric. Anim. Sci., 1967, vol. 23, No. 4, pp. 599–604.

Chemical Abstract, No. 67(25)115916d, *Titrimetric determination of L–Ascorbic Acid in Colored Solutions. I.V. Acerola Cherries and Their Concomitant Use in Fruit Juices*, Authors: Rudolf Fischer, G. Freise; Journal: Dtsch. Apoth.–Ztg.; 1967, vol. 107, No. 34, pp. 1175–1176.

Chemical Abstract, No. 66(21)92405z, *Factors Affecting Ascorbic Acid Content of the Acerola (Malphigia Glabra)*, Authors: H.Y. Nakasone, R.K. Miyashita, George M. Yamane, Journal: Proc. Am. Soc. Hortic. Sci., 1966, vol. 89, pp. 161–166.

Chemical Abstract, No. 66(5)18134u, *Ascorbic Acid Content of Acerola Fruits and Acerola Powder, Ascorbic Acid Determination in the Presence of Reductones*, Author: Annelies Schillinger, Journal: Z. Lebensm.–Unters. Forsch, 1966, vol. 131, No. 2.

SKIN WHITENER COMPOSITION CONTAINING ACEROLA CHERRY FERMENTATE

BACKGROUND OF THE INVENTION

The present invention relates to a skin whitener composition containing acerola cherry fermentate for external use and to a method of whitening skin by topically applying a composition containing an effective amount of acerola cherry fermentate.

In Asia, most women desire whiter skin because of traditional beliefs that white skin denotes nobility and aristocracy. Skin color is primarily determined by the amount of melanin present in the skin. Thus, in recent years, cosmetic compositions have been developed to reduce the amount of melanin in the skin and therefore, whiten the skin. These development efforts have focused on whitening agents that inhibit the function and activity of tyrosinase, which plays a key role in the biosynthesis of melanin. For example, it has been proposed to incorporate into cosmetic compositions tyrosinase activity inhibitors such as hydroquinone, vitamin C and its derivatives, kojic acid, arbutin, glutathione, cysteine, and mulberry extract, among others.

Alternatively, U.S. Pat. No. 5,262,153 describes the use of lactic acid and particular derivatives of lactic acid in amounts of 5 weight percent or greater to suppress the formation of tyrosinase rather than inhibiting its activity after its formation.

Despite the efficacy of the above compounds in producing a whiter skin, their effects can be improved by adding acerola cherry fermentate to the presently known whitening agents. The present inventors have found that by adding acerola cherry fermentate to known whitening agents, their skin whitening effects can be enhanced.

Although Japanese Laid-open applications 2-200610 and 70-61915 teach that an extract obtained from fruits of acerola may be incorporated into cosmetics, those applications teach that the acerola cherry extract contains vitamin C or ascorbic acid. In fact, application no. 2-200610 describes the extract as containing at least 1% L-ascorbic acid and it is the presence of the L-ascorbic acid that provides the whitening effect. This is not surprising since it is well known that L-ascorbic acid provides a whitening effect. The acerola cherry fermentate used in the present invention, however, is substantially free from ascorbic acid and thus its ability to enhance the whitening effect of known whitening agents is surprising and unexpected.

SUMMARY OF THE INVENTION

It is an object of the present invention to provide compositions suitable for external application that prevent or inhibit the formation of melanin in the skin or the like and whiten the skin that include acerola cherry fermentate. Another object is to enhance and accelerate the development of the whitening and beautifying effect exhibited by known whitening agents by incorporating an acerola cherry fermentate and, more particularly, an acerola cherry fermentate which is substantially free from ascorbic acid and contains, at most, a minor amount of organic acids, particularly carboxylic acids.

The present invention also includes a method of whitening the skin that comprises topically applying to the skin an acerola cherry fermentate in an amount and for a period of time sufficient to visibly whiten the skin. A preferred method comprises topically applying to the skin a composition comprising acerola cherry fermentate and one or more known whitening agents.

The known whitening agents may be selected from the group consisting of tyrosinase inhibitors, or free radical scavengers, and mixtures thereof.

Examples of suitable tyrosinase inhibitors include, but are not limited to, kojic acid and its derivatives, arbutin and its derivatives, Licorice extract and its derivatives, ascorbic acid and its derivatives, and hydroquinone and its derivatives. Examples of suitable free radical scavengers include, but are not limited to Licorice extract and its derivatives, vitamin E and its derivatives, vitamin A and its derivatives, vitamin C and its derivatives, Rosemary extract and its derivatives and superoxide dismutase.

The term "substantially free from ascorbic acid" as used in the specification and accompanying claims means that any ascorbic acid present in the acerola cherry fermentate is present in an amount no greater than about 1% by weight, preferably no greater than about 0.1%, and more preferably no greater than about 0.01% of the acerola cherry fermentate. Most preferably, the ascorbic acid, if present, is present in an amount no greater than about 0.005% of the acerola cherry fermentate. As taught by Japanese application no. 2-200610, an amount of ascorbic acid less than about 1% should not contribute any whitening effect.

The term "minor amount of organic acids" and "minor amount of carboxylic acids" as used in the specification and accompanying claims means that any organic acid or carboxylic acid, which includes saturated and unsaturated carboxylic and dicarboxylic acids, hydroxymonocarboxylicic acids, hydroxydicarboxylic acids, and hydroxytricarboxylic acids, is present in an amount no greater than about 5% by weight, preferably no greater than about 3%, and more preferably, no greater than about 2% of the acerola cherry fermentate.

In the whitener composition according to the present invention, the amount of acerola cherry fermentate to be used can not be absolutely specified because it varies according to the form of preparation. However, it is generally used in an amount from about 0.01% to about 50%, more generally from about 0.01% to about 10%. Preferably the acerola cherry fermentate is used in an amount from about 0.05% to about 2%, more preferably from about 0.1% to about 1% based on the whole weight of the whitener composition.

When the acerola cherry fermentate is combined with known whitening agents, it is preferably combined such that the ratio of the acerola cherry fermentate to the known whitening agent is from about 1:100 to about 100:1, preferably from about 1:50 to about 50:1, more preferably from about 1:10 to about 10:1. Most preferably, the ratio of acerola cherry fermentate to known whitening agent is from about 1:5 to about 5:1.

It is noted that, unless otherwise stated, all percentages given in this specification and the appended claims refer to percentages by weight.

DETAILED DESCRIPTION OF THE INVENTION

In accordance with the present invention, a skin whitener composition is provided and comprises acerola cherry fermentate as an active ingredient. In another aspect, the skin whitener composition comprises one or more whitening agents, and acerola cherry fermentate to enhance the whitening effect of the whitening agents.

The acerola cherry is not, in fact, a true cherry but has come to include the cherry-like berries that are produced by any of several shrubs of the Malpighia family. These cherry-like berries are also known by other names depending on where they are produced, for instance, West Indian cherry, Barbados cherry, Surinam cherry, and Cereza. The term "acerola cherry" as used in the specification and appended claims is intended to be generic for all of these different berries of the Malpighia family.

Acerola cherries contain vitamin C and, as discussed in U.S. Pat. Nos. 3,012,942 and 3,086,915 and Japanese Laid-open application 2-200610, it is known to extract vitamin C from them for several different uses. In the present invention, however, the acerola cherry fermentate is substantially free from any substantial amount of vitamin C (ascorbic acid or its derivatives). In other words, the acerola cherry does not contain more than about 1% by weight, preferably no greater than about 0.1%, and more preferably no greater than about 0.01% of the acerola cherry fermentate. Most preferably, the ascorbic acid, if present, is present in an amount no greater than about 0.005% of the acerola cherry fermentate.

In addition, the acerola cherry fermentate used in the present invention contains only a minor amount of organic acid, particularly carboxylic acids, which includes saturated and unsaturated carboxylic and dicarboxylic acids, hydroxy-monocarboxylicic acids, hydroxydicarboxylic acids, and hydroxytricarboxylic acids. In particular, any organic acid or carboxylic acid present in the acerola cherry fermentate is present in an amount no greater than about 5% by weight, preferably no greater than about 3%, and more preferably no greater than about 2% of the acerola cherry fermentate.

The acerola cherry fermentate can be made in any suitable manner to achieve an extract that is substantially free of ascorbic acid and contains only a minor amount of organic acids, preferably less than about 5% of organic acids. The raw acerola cherry used to make the fermentate may be brown, green, yellow, red or a mixture of two or more, depending upon the availability.

Preferably, the acerola cherry fermentate is obtained from Collaborative Laboratories (NY) and it is believed that the process for making the Acerola cherry fermentate useful in the composition of the present invention is as follows. A cherry extract is prepared by washing the bulk cherries, pitting them and then reducing them to a puree, which is subjected to shearing and extraction with water whereby a filtrate is produced. Thereafter, the filtrate is fermented using a bacteria, preferably a bacteria from the lactobacillus family, to produce a fermentate that is separated from the bulk filtrate. The separated fermentate is the acerola cherry fermentate useful in the present invention.

In the whitener composition according to the present invention, the amount of acerola cherry fermentate to be used can not be absolutely specified because it varies according to the form of the preparation. It is, however, generally used in an amount from about 0.01% to about 50%, more generally from about 0.01% to about 10%. Preferably the acerola cherry fermentate is used in an amount from about 0.05% to about 2%, more preferably from about 0.1% to about 1% based on the whole weight of the whitener composition.

As noted above, the compositions of the present invention include acerola cherry fermentate and one or more whitening agents. The whitening agents useful in the present invention are believed to include all the known whitening agents and those that may be developed in the future. The whitening agents are selected from the group consisting of tyrosinase inhibitors and free radical scavengers. Examples of suitable tyrosinase inhibitors include, but are not limited to, kojic acid and its derivatives, arbutin and its derivatives, licorice extract and its derivatives, ascorbic acid and its derivatives, and hydroquinone and its derivatives. Examples of suitable free radical scavengers include, but are not limited to licorice extract and its derivatives, vitamin E and its derivatives, vitamin A and its derivatives, vitamin C and its derivatives, Rosemary extract and its derivatives and superoxide dismutase.

Although it may not be possible to identify and list all known whitening agents, the following whitening agents may be mentioned and for purposes of the present invention are preferred: hydroquinone, vitamin C and its derivatives, kojic acid and its derivatives, arbutin, bearberry extract, glutathione, lemon extract, cucumber extract, mulberry extract, licorice extract, mercaptosuccinic acid, and their derivatives. Preferred whitening agents are selected from the group consisting of kojic acid, derivatives of kojic acid, arbutin, derivatives of arbutin, bearberry extract, lemon extract, cucumber extract, vitamin C and its derivatives, and mercaptosuccinic acid.

The kojic acid or its esters may be represented by the formula:

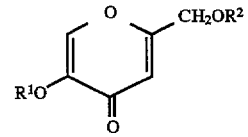

wherein $R^1$ and $R^2$ are the same or different, and each is hydrogen atom or an acyl group of 3 to 20 carbon atoms.

Non-exclusive examples of the esters are, for instance, kojic acid monoesters such as kojic acid monobutyrate, kojic acid monocaprate, kojic acid monopalmitate, kojic acid monostearate, kojic acid monocinnamoate and kojic acid monobenzoate; kojic acid diesters such as kojic acid dibutyrate, kojic acid dipalmitate, kojic acid distearate and kojic acid dioleate. A preferred monoester is an ester in which a OH group at 5-position of kojic acid is esterified. Esterification can improve stabilities against pH or sun light, while maintaining a melanin synthesis-inhibiting activity equal to that of kojic acid.

Non-exclusive examples of the vitamin C derivatives are, for instance, alkyl esters of L-ascorbic acid such as L-ascorbyl palmitate, L-ascorbyl isopalmitate, L-ascorbyl dipalmitate, L-ascorbyl isostearate, L-ascorbyl distearate, L-ascorbyl diisostearate, L-ascorbyl myristate, L-ascorbyl isomyristate, L-ascorbyl 2-ethylhexanoate, L-ascorbyl di-2-ethylhexanoate, L-ascorbyl oleate and L-ascorbyl dioleate; phosphates of L-ascorbic acid such as L-ascorbyl-2-phosphate and L-ascorbyl-3-phosphate; sulfates of L-ascorbic acid such as L-ascorbyl-2-sulfate and L-acorbyl-3-sulfate; their salts with alkaline earth metals such as calcium and magnesium. They can be used alone or in a mixture of two or more.

The composition of the present invention may be prepared in various forms. For example, it may be in the form of a cosmetic preparation such as cream, cosmetic lotion, pack or powder, or as an emulsion, lotion, liniment or ointment. In each formulation, various known conventional cosmetic ingredients may be incorporated. For example, cosmetic ingredients such as alcohols, fats and oils, surfactants, fatty acids, silicone oils, humectants, moisturizers, viscosity modifiers, emulsifiers, stabilizers, coloring agents, and perfumes may be included.

The acerola cherry fermentate is mixed with the known whitening agents such that the ratio of the acerola cherry fermentate to the known whitening agent is from about 1:100 to about 100:1, preferably from about 1:50 to about 50:1, more preferably from about 1:10 to about 10:1. Most preferably, the ratio of acerola cherry fermentate to known whitening agent is from about 1:5 to about 5:1.

The composition according to the present invention achieves its enhanced whitening effect due to the synergism of acerola cherry fermentate with other substances having a known whitening effect. Although the exact mechanism by which the acerola cherry enhances the whitening effect of known whitening agents is not known, it is believed that the acerola cherry fermentate complexes with or chelates the copper present in tyrosinase and thus inhibits its synthesis. As a result the production of melanin is inhibited.

In another aspect of the composition of the present invention there is provided an improved skin whitening composition of the type containing skin whitening agents wherein the improvement comprises adding acerola cherry fermentate, as fully defined above.

The present invention also contemplates a method of enhancing the skin whitening effect of known whitening agents that comprises adding acerola cherry fermentate to the known whitening agents.

In another aspect of the present invention, a method of whitening skin is provided and comprises topically applying to the skin acerola cherry fermentate in an amount and for a period of time sufficient to visibly whiten the skin. More preferably, the method comprises topically applying to the skin a composition comprising acerola cherry fermentate and a pharmaceutically acceptable carrier. The term "pharmaceutically acceptable" means those drugs, medicaments, or inert ingredients which are suitable for use in contact with the tissues of humans and lower animals without undue toxicity, incompatibility, instability, irritation, and the like, commensurate with a reasonable benefit/risk ratio.

To demonstrate the enhancement of known whitening agents by the presence of the acerola cherry fermentate of the present invention, the following test was conducted.

A buffer solution A containing 50 mM sodium acetate was prepared to yield a 6.8 pH. A tryosine solution was prepared by adding 15 mg of tyrosine to 100 ml of buffer solution A. A tyrosinase solution was prepared by adding 11.5 mg tyrosinase from mushroom (Serva Art. 37618, 72 µ/mg) in 1.2 ml. of buffer solution A.

A test tube was charged with 2.7 ml of buffer solution A and 0.4 ml. water to define a blank. Similarly, another test tube was charged with 2.7 ml. of the tyrosine solution, 0.3 ml of water, and 0.1 ml of the tyrosinase solution to define a reference. The absorbency of the reference was measured at 475 nm over a period of time with a spectrophotometer and the absorbancy was set to zero.

The following examples present the results of the inhibition of the tyrosinase as measured in the above manner by several whitening agents, alone and with the acerola cherry fermentate.

EXAMPLE 1

A test tube was charged with 2.7 ml of the tyrosine solution, 0.1 ml. of the tyrosinase solution and 0.02% of mercaptosuccinic acid together with 0.5% acerola cherry fermentate. Comparative example 1 contained 2.7 ml of the tyrosine solution, 0.1 ml. of the tyrosinase solution and only 0.02% mercaptosuccinic acid. The absorbancy of example 1 and comparative example 1 were measured at 0.5 hours and 24 hours. The percent inhibition of the tyrosinase of example 1 was calculated as follows:

$$\% \text{ inhibition} = 100 \times \left[ 1 - \frac{\left( \begin{array}{c} \text{absorbancy of} \\ \text{Example 1} \end{array} - \begin{array}{c} \text{absorbancy} \\ \text{of reference} \end{array} \right)}{\begin{array}{c} \text{absorbancy} \\ \text{of reference} \end{array} - \begin{array}{c} \text{absorbancy} \\ \text{of blank} \end{array}} \right]$$

The percent inhibition of comparative example 1 was calculated in a similar manner.

At 0.5 hours, example 1 had a 92% inhibition while comparative example 1 had 95% inhibition. But at 24 hours, example 1 had 91% inhibition while comparative example 1 had only 77% inhibition.

EXAMPLE 2

A test tube was charged with 2.7 ml of the tyrosine solution, 0.1 ml. of the tyrosinase solution and 0.5% of kojic acid together with 0.5% acerola cherry fermentate. Comparative example 2 contained 2.7 ml of the tyrosine solution, 0.1 ml. of the tyrosinase solution and 1.0% kojic acid. The absorbency of each was measured at 0.5 hours and at 24 hours in the same manner as described above. Table 1 presents the results.

TABLE 1

| | Percent Inhibition (0.5 hours) | Percent Inhibition (24 hours) |
|---|---|---|
| Example 2 | 92 | 93 |
| Comparative Example 2 | 91 | 92 |

EXAMPLES 3 and 4

A test tube was charged with 2.7 ml of the tyrosine solution, 0.1 ml. of the tyrosinase solution and 0.5% Fadeout (active ingredient is arbutin, which is derived from bearberry) together with 0.5% acerola cherry fermentate to define example 3. For example 4 a test tube was charged with 2.7 ml of the tyrosine solution, 0.1 ml. of the tyrosinase solution and 0.33% Fadeout, 0.33% Uninontan (active ingredients include lemon and cucumber extract), and 0.33% acerola cherry fermentate. Comparative example 3 contained 2.7 ml of the tyrosine solution, 0.1 ml. of the tyrosinase solution and contains 1.00% Fadeout. The absorbency of examples 3 and 4 and comparative example 3 were measured at 0.5 hours and at 24 hours in the same manner as described above. Table 2 presents the results.

TABLE 2

| | Percent Inhibition (0.5 hours) | Percent Inhibition (24 hours) |
|---|---|---|
| Example 3 | 87 | 86 |
| Example 4 | 92 | 92 |
| Comparative Example 3 | 81 | 88 |

EXAMPLE 5

A test tube was charged with 2.7 ml of the tyrosine solution, 0.1 ml. of the tyrosinase solution and 0.5% Uninontan and 0.5% acerola cherry fermentate to define example 5. Comparative example 5 contained 2.7 ml of the tyrosine solution, 0.1 ml. of the tyrosinase solution and 1.00% Uninontan. The absorbency of each was measured at 0.5 hours and at 24 hours in the same manner as described above. Table 3 presents the results.

TABLE 3

|  | Percent Inhibition (0.5 hours) | Percent Inhibition (24 hours) |
|---|---|---|
| Example 5 | 73 | 62 |
| Comparative Example 5 | 66 | 55 |

EXAMPLE 6

A test tube was charged with 2.7 ml of the tyrosine solution, 0.1 ml. of the tyrosinase solution and 5% willowbark extract and 0.33% acerola cherry fermentate to define example 6. Comparative example 6 contained 2.7 ml of the tyrosine solution, 0.1 ml. of the tyrosinase solution and 5.00% willowbark extract. The absorbency of each was measured at 0.5 hours and at 24 hours in the same manner as described above. Table 4 presents the results.

TABLE 4

|  | Percent Inhibition (0.5 hours) | Percent Inhibition (24 hours) |
|---|---|---|
| Example 6 | 85 | 75 |
| Comparative Example 6 | 83 | 15 |

Based on the above tests it is believed that compositions containing acerola cherry extract would be efficacious in whitening skin.

The following is an example of a composition according to the present invention.

| INGREDIENT | PERCENTAGE (weight) |
|---|---|
| Water | 88.11 |
| Carbopol 1342 | 0.20 |
| Glycerin | 4.80 |
| Triethanolamine | 0.20 |
| Squalane | 3.00 |
| Sorbitan Laurate | 0.20 |
| Soybean Oil | 1.00 |
| Acerola Cherry Fermentate | 0.33 |
| Uninontan | 0.33 |
| Fadeout | 0.33 |
| Orange Extract | 1.00 |
| Phenonip | 0.50 |

It should be understood that a wide range of changes and modifications can be made to the embodiments described above. It is therefore intended that the foregoing description illustrates rather than limits this invention, and that it is the following claims, including all equivalents, which define this invention.

What is claimed:

1. A composition for topical use which has a melanin synthesis-inhibiting activity, comprising acerola cherry fermentate and a whitening agent, wherein the acerola cherry fermentate is substantially free of ascorbic acid.

2. The whitening composition of claim 1 which is a preparation selected from the group consisting of cream, ointment, foam, lotion, plaster, tablets, granules, or emulsion.

3. In a skin whitening cosmetic composition comprising a skin whitening agent, the improvement comprising an effective amount of acerola cherry fermentate.

4. The composition of claim 3 wherein the skin whitening agent is selected from the group of tryosinase inhibitors, free radical scavengers, and mixtures thereof.

5. The composition of claim 4 wherein the skin whitening agent is selected from the group consisting of extract of bearberry, arbutin, lemon extract, cucumber extract, mercaptosuccinic acid, kojic acid, derivatives of kojic acid, vitamin C and derivatives of vitamin C and mixtures thereof.

6. The composition of claim 5 wherein the skin whitening agent is mixture of arbutin and a mixture of lemon and cucumber extract, and wherein the ratio of acerola cherry fermentate to arbutin to the mixture of lemon and cucumber extract is about 1:1:1.

7. A method of visibly whitening human skin comprising topically applying to the skin a composition comprising acerola cherry fermentate that is substantially free of ascorbic acid and a whitening agent, the composition applied in an amount and for a period of time sufficient to visibly whiten the skin.

8. A method of visibly whitening human skin comprising topically applying to the skin a composition in an amount and for a period of time sufficient to visibly whiten the skin, the composition comprising acerola cherry fermentate and a whitening agent, wherein the acerola cherry fermentate is substantially free of ascorbic acid.

9. The method of claim 8 wherein the whitening agent is selected from the group consisting of tyrosinase inhibitors, free radical scavengers, and mixtures thereof.

* * * * *